US008501680B2

(12) United States Patent
Weber et al.

(10) Patent No.: US 8,501,680 B2
(45) Date of Patent: Aug. 6, 2013

(54) ANTAGONISTS AGAINST INTERACTION OF PF4 AND RANTES

(75) Inventors: Christian Weber, Aachen (DE); Philipp Von Hundelshausen, Aachen (DE); Rory Koenen, Ubach-Palenberg (DE)

(73) Assignee: RWTH Aachen, Aachen (DE)

( * ) Notice: Subject to any disclaimer, the term of this patent is extended or adjusted under 35 U.S.C. 154(b) by 0 days.

(21) Appl. No.: 13/315,088

(22) Filed: Dec. 8, 2011

(65) Prior Publication Data

US 2012/0077733 A1 Mar. 29, 2012

Related U.S. Application Data

(62) Division of application No. 12/090,010, filed as application No. PCT/EP2006/009790 on Oct. 11, 2006, now Pat. No. 8,110,552.

(30) Foreign Application Priority Data

Oct. 14, 2005 (DE) .......................... 10 2005 049 637

(51) Int. Cl.
*A61K 38/10* (2006.01)
*A61K 38/12* (2006.01)
*C07K 7/64* (2006.01)
*C07K 14/435* (2006.01)

(52) U.S. Cl.
USPC .......... 514/1.9; 514/21.1; 514/21.4; 530/300; 530/317; 530/326

(58) Field of Classification Search
None
See application file for complete search history.

(56) References Cited

U.S. PATENT DOCUMENTS

| | | | | |
|---|---|---|---|---|
| 6,168,784 | B1 * | 1/2001 | Offord et al. | 424/85.1 |
| 6,534,626 | B1 * | 3/2003 | Oravecz et al. | 530/300 |
| 8,110,552 | B2 | 2/2012 | Weber et al. | |

FOREIGN PATENT DOCUMENTS

| | | |
|---|---|---|
| DE | 10014516 | 9/2001 |
| WO | WO-9806751 A1 * | 2/1998 |
| WO | WO-00-27880 | 5/2000 |
| WO | WO-2004-065406 A2 | 8/2004 |
| WO | WO-2004-065406 A3 | 8/2004 |
| WO | WO-2007-042263 | 4/2007 |
| WO | WO-2010-042548 | 4/2010 |

OTHER PUBLICATIONS

Anders et al. "CC chemokine ligand/RANTES chemokineantagonists aggravate glomerulonephritis despite reduction of glomerular leukocyte infiltration." *J Immunol*, 2003, 170:5658-5666.
Appay et al. "RANTES: a versatile and controversial cytokine." *TRENDS Immunobiol*, 2001, 22(2):83-87.
Dawson et al. "Synthesis of Native Proteins by Chemical Ligation." *Annu Rev. Biochem*, 2000, 69:923-960.
Hacking et al. "Protein synthesis by native chemical ligation: Expanded scope by using straightforward methodology." *Proc. Natl. Acad. Sci. USA*, 96:10068-10073.
Huo et al. "Circulating activated platelets exacerbate atherosclerosis in mice deficient in apolipoprotein E." *Nature Med*, 2003, 9(1):61-67.
Koenen et al. "Disrupting functional interactions between platelet chemokines inhibits atherosclerosis in hyperlipidemic mice." *Nature Med*, 2009, 15(1):97-103.
Nesmelova et al. "CXC and CC chemokines form mixed heterodimers." *J Biol Chem*, 2008, 283(35):24155-24166.
Vandercappellen et al. "The role of the CXC chemokines platelet factor-4 (CXCL4/PF-4) and its variant (CXCL4L1/PF-4var) in inflammation, angiogenesis and cancer." *Cytokine Growth Factor Rev*, 2011, 22:1-18.
Veillard et al. "Antagonism of RANTES Receptors Reduces Atherosclerolic Plaque Formation in Mice." *Circulation Research*; 2004, 94:253-261.
von Hundelshausen et al. "Heterophillic interactions of platelet factor 4 and RANTES promote monocyte arrest on endothelium." *Blood*, Feb. 2005, 105(3):924-930.
Weber, Christian. "Platelets and Chemokines in Atherosclerosis: Partners in Crime." *Circ Res.*, 2005, 96:612-616.
PCT/EP2006/009790 Internation Search Report and Written Opinion dated Feb. 14, 2007.
CA2648649 Office Action dated Oct. 6, 2011.
IL190820 Official Action date Nov. 28, 2011.
PH12008501104 Exam Report dated May 25, 2012.

* cited by examiner

*Primary Examiner* — Bridget E Bunner
(74) *Attorney, Agent, or Firm* — Wilson, Sonsini, Goodrich & Rosati

(57) ABSTRACT

The invention relates to polypeptides of amino acid sequence SEQ ID NO: 1 according to formula (1), the use thereof for producing a medicament, and medicaments for the treatment of diseases related to monocyte recruitment.

14 Claims, No Drawings

ANTAGONISTS AGAINST INTERACTION OF PF4 AND RANTES

This application is a divisional application of U.S. patent application Ser. No. 12/090,010, filed Jul. 9, 2008, which issued as U.S. Pat. No. 8,110,552, on Feb. 7, 2012, which is a national phase entry of International Patent Application Number PCT/EP2006/009790, filed Oct. 11, 2006, which published as WIPO Publication Number WO 2007/042263 on Apr. 19, 2007, which claims priority from DE 102005049637.7, filed on Oct. 14, 2005.

The instant application contains a Sequence Listing which has been submitted in ASCII format via EFS-web and is hereby incorporated by reference in its entirety. Said ASCII copy is named 36591-703-401seqlisting.txt and is 6,356 bytes in size.

The invention relates to polypeptides, their pharmacologically acceptable salts, derivatives and/or conjugates, their use for production of a pharmaceutical drug and said pharmaceutical drug. The polypeptides are suitable for treatment of diseases associated with recruitment of monocytes.

Arteriosclerosis of arterial vessels forms the morphological background of cardiovascular diseases. The initial recruitment of monocytes is of crucial importance here for the genesis of the early arteriosclerotic lesion. Adhesion of monocytes to the endothelium, the so-called monocyte arrest stands at the beginning of the pathogenesis of cardiovascular diseases such as arteriosclerosis, stenoses and thromboses. It is known that chemokines such as RANTES (regulated on activation, normal T cell expressed and secreted) are associated with these processes as signal molecules.

Primary and secondary prevention known in the state of the art include mainly a lipid lowering treatment and inhibition of platelets aggregation and activation by medicines such as aspirin or clopidogrel. The disadvantage of treatment with these medicines is, first of all, that they have only a low specificity and, secondly, that these medicines entail serious adverse effects such as myopathies and an elevated risk of hemorrhage.

In addition, the use of RANTES peptide antagonists is known in the state of the art. For example, DE 100 14 516 A1 discloses the use of metRANTES as an antagonist to the RANTES receptor CCR1. A disadvantage in use of these antagonists is that chemokines are involved as signal molecules in a number of physiological processes so that an unforeseeable number of physiological processes are influenced by the use of such an antagonist and numerous side effects and sequelae may occur.

The object of the present invention was therefore to make available agents that would overcome at least one of the disadvantages of the state of the art. In particular, the object of the present invention was to make available agents that would have an improved specificity.

This object is achieved by a polypeptide, its pharmacologically acceptable salts, derivatives and/or conjugates, whereby the polypeptide has an amino acid sequence SEQ ID NO: 1 according to formula (1) as given below:

(SEQ ID NO: 1)
C-$X_1$-$X_2$-YFYTS-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-C  (1)

wherein:
$X_1$ is selected from the group comprising lysine, glutamine, arginine, histidine and/or asparagine or an amino acid deletion
$X_2$ is selected from the group comprising glutamic acid, aspartic acid and/or glutamine or an amino acid deletion
$X_3$ is selected from the group comprising glycine, serine and/or alanine
$X_4$ is selected from the group comprising lysine, leucine and/or arginine
$X_5$ is selected from the group comprising serine, cysteine, glycine and/or threonine
$X_6$ is selected from the group comprising serine, glycine and/or threonine
$X_7$ is selected from the group comprising asparagine and/or glutamine
$X_8$ is selected from the group comprising proline, tyrosine and/or glycine
$X_9$ is selected from the group comprising glycine, alanine and/or serine
$X_{10}$ is selected from the group comprising isoleucine, valine and/or asparagine
$X_{11}$ is selected from the group comprising valine, isoleucine and/or asparagine
$X_{12}$ is selected from the group comprising phenylalanine, tyrosine, isoleucine, valine, leucine and/or methionine
$X_{13}$ is selected from the group comprising isoleucine, valine, leucine, methionine and/or phenylalanine
$X_{14}$ is selected from the group comprising threonine, glycine, alanine, serine and/or tyrosine
$X_{15}$ is selected from the group comprising arginine, lysine, glutamine, histidine and/or asparagine or an amino acid deletion.

The inventive polypeptides are advantageously suitable as an antagonist to the interaction between RANTES and platelet factor 4.

The term "antagonist to the interaction between RANTES and platelet factor 4" is understood in the sense of the present invention to include peptides, proteins or other compounds which can function as an antagonist to the interaction between the chemokines RANTES and platelet factor 4.

It has surprisingly been found that the inventive polypeptides can have a specific effect on the recruitment of monocytes mediated by the interaction of the chemokines RANTES and platelet factor 4 (PF4). It is a particular advantage here that the inventive polypeptides have little or no effect on the numerous functions of the chemokines. It is advantageous in particular that selective blocking of the recruitment of monocytes can have an effect on endothelium in particular.

The term "recruitment of monocytes" includes in the sense of the present invention the meaning of migration of monocytes into, through and out of the endothelium, their adhesion and propagation, e.g., in endothelial gaps. The adhesion of monocytes is also referred to as monocyte adhesion and/or as monocyte arrest when the adhesion takes place in shearing flow as under physiological conditions, e.g., in blood capillaries, microvascular or arterial circulation.

It is a great advantage that the inventive polypeptides can provide a high specificity and have little or no adverse effects on the numerous metabolic processes mediated by the chemokines RANTES and PF4, e.g., the immune system or the coagulation system. In particular, by administering the inventive polypeptides, a bleeding risk can be prevented as with traditional medication in cardiovascular diseases.

In the present context, using the conventional one-letter code of amino acids, "C" stands for cysteine and accordingly "Y" stands for tyrosine, "F" stands for phenylalanine, "T" stands for threonine and "S" stands for serine.

The inventive polypeptide has one cysteine radical on the amino-terminal end and another on the carboxy-terminal end, which can make possible cyclization of the polypeptide. It is especially advantageous that a cyclized polypeptide has an improved stability. The inventive polypeptide may have a longer-lasting effect and therefore a smaller amount may be used accordingly.

The term "polypeptide" in the sense of the present invention is understood to refer to synthetic or nonsynthetic peptide compounds as well as purified and modified fragments of natural proteins, native forms or recombinant peptides or proteins. Likewise, the term "polypeptide" in the sense of the present invention includes pharmacologically acceptable salts, pharmacologically acceptable derivatives and/or conjugates of the corresponding polypeptide.

Preferred pharmacologically acceptable derivatives include, for example, the esters, amides, N-acyl and/or O-acyl derivatives, carboxylated, acetylated, phosphorylated and/or glycosylated polypeptides. Preferred conjugates include, for example, sugar or polyethylene glycol conjugates, biotinylated radioactive or fluorescence-labeled polypeptides.

The polypeptide preferably has a length of at most 25 amino acids. The polypeptide preferably has a number of amino acids in the range of $\geq 15$ to $\leq 25$ amino acids, preferably in the range of $\geq 15$ to $\leq 22$ amino acids. It has been found as part of the present investigation that the length of the polypeptide can have an influence on its efficacy. In particular, it is surprising that an amino acid sequence of this length can trigger inhibition of monocyte arrest.

In preferred embodiments the polypeptide has a number of amino acids in the range of $\geq 18$ to $\leq 23$ amino acids, more preferably in the range of $\geq 18$ to $\leq 22$ amino acids; in especially preferred embodiments the polypeptide has in the range of $\geq 19$ to $\leq 22$ amino acids, and in more preferred embodiments the polypeptide has in the range of $\geq 20$ to $\leq 21$ amino acids. Most especially preferably the polypeptide has 22 amino acids. The term "number of amino acids" in the sense of the present invention of course also includes the meaning of the length of the amino acid sequence of the polypeptide.

In preferred embodiments of the inventive polypeptide, $X_1$ corresponds to lysine or in position $X_1$ of the amino acid sequence there is a deletion, especially preferably $X_1$ corresponds to the amino acid lysine. Furthermore, $X_2$ in preferred embodiments of the polypeptide corresponds to the amino acid glutamic acid or is an amino acid deletion. $X_2$ especially preferably corresponds to the amino acid glutamic acid. A polypeptide with a deletion in position $X_1$ and/or $X_2$ may surprisingly manifest an antagonistic effect. It is possible to provide for $X_1$ and $X_2$ to correspond to an amino acid deletion.

$X_3$ preferably corresponds to a small, neutral and flexible amino acid. In preferred embodiments of the polypeptide, $X_3$ is selected from the group comprising glycine and/or serine; $X_3$ especially preferably corresponds to the amino acid glycine. It has been found that these amino acids have a positive influence in the stability of the structure of the polypeptide. Such an increase in the stability is especially advantageous because an increased stability of the polypeptide makes it possible to prolong the interaction of the polypeptide with the chemokine PF4. An improved stabilization of the peptide can thus enhance the antagonistic properties of the polypeptide.

In preferred embodiments of the polypeptide, $X_4$ corresponds to the amino acid lysine.

$X_5$ is preferably selected from the group comprising serine, glycine and/or threonine. In especially preferred embodiments of the polypeptide, $X_5$ corresponds to serine. This embodiment of the polypeptide may advantageously result in an improvement in the solubility of the polypeptide. An increase in the solubility of the polypeptide may result in particular in an increase in the applicability of the polypeptide in water. This allows a simplification of the administration of the polypeptide in the usual administration methods based on water. In addition, an improved dispersibility of the polypeptide in the aqueous systems of the body, in particular in blood, can be made available through this improved solubility of the polypeptide.

$X_6$ preferably corresponds to the amino acid serine. In other preferred embodiments of the polypeptide, $X_7$ corresponds to the amino acid asparagine.

$X_8$ preferably corresponds to an amino acid selected from the group comprising proline and/or tyrosine. $X_8$ especially preferably corresponds to the amino acid proline.

In especially preferred embodiments of the polypeptide, $X_9$ corresponds to glycine. It has been found that the amino acid glycine in this position in the amino acid sequence can lead to a surprisingly stable polypeptide compound.

$X_{10}$ and $X_{13}$ independently of one another are preferably selected from the group comprising valine and/or isoleucine. In preferred embodiments of the polypeptide, $X_{10}$ corresponds to isoleucine. In additional preferred embodiments of the polypeptide, $X_{13}$ corresponds to isoleucine. In especially preferred embodiments of the polypeptide, $X_{10}$ and $X_{13}$ correspond to isoleucine. It has been found that isoleucine in positions $X_{10}$ and $X_{13}$ of the polypeptide can contribute toward an increased stability of the conformation of the polypeptide.

$X_{11}$ preferably corresponds to the amino acid valine. $X_{12}$ is preferably selected from the group comprising phenylalanine and/or tyrosine, especially preferably $X_{12}$ corresponds to the amino acid phenylalanine. $X_{14}$ preferably corresponds to the amino acid threonine.

$X_{15}$ preferably corresponds to arginine; also, an amino acid deletion may also be provided in position $X_{15}$ in the amino acid sequence. The amino acid deletions preferably involve $X_1$, $X_2$ and/or $X_{15}$. One of the amino acids $X_1$, $X_2$ or $X_{15}$ may preferably be deleted, but it is also possible for amino acid deletions to be provided in positions $X_1$ and $X_2$. In other embodiments deletions may be provided in positions $X_1$, $X_2$ and $X_{15}$. In preferred embodiments of the polypeptide, no deletions are provided in the area of amino acids $X_3$ through $X_{14}$.

In preferred embodiments of the polypeptide, $X_5$ corresponds to the amino acid serine, $X_9$ corresponds to glycine, $X_{10}$ corresponds to leucine and/or $X_{13}$ corresponds to isoleucine. In especially preferred embodiments of the polypeptide, $X_5$ corresponds to the amino acid serine, $X_9$ corresponds to glycine, $X_{10}$ corresponds to isoleucine and $X_{13}$ corresponds to isoleucine. It has been found that a polypeptide in which $X_5$ corresponds to the amino acid serine, $X_9$ corresponds to glycine, $X_{10}$ corresponds to isoleucine and $X_{13}$ corresponds to isoleucine has an especially good antagonist potential.

In another preferred embodiment of the polypeptide, $X_5$ corresponds to the amino acid serine, $X_9$ corresponds to glycine, $X_{10}$ corresponds to isoleucine, $X_{13}$ corresponds to isoleucine, $X_1$ corresponds to an amino acid deletion and/or $X_{15}$ corresponds to an amino acid deletion. In especially preferred embodiments of the polypeptide, $X_5$ corresponds to the amino acid serine, $X_9$ corresponds to glycine, $X_{10}$ corresponds to isoleucine, $X_{13}$ corresponds to isoleucine, $X_1$ corresponds to an amino acid deletion and $X_{15}$ corresponds to an amino acid deletion. This polypeptide may also have an especially good antagonist potential.

In an even more preferred embodiment of the polypeptide, $X_5$ corresponds to the amino acid serine, $X_8$ corresponds to tyrosine, $X_9$ corresponds to glycine, $X_{10}$ corresponds to isoleucine, $X_{13}$ corresponds to isoleucine, $X_1$ corresponds to an amino acid deletion and/or $X_{15}$ corresponds to an amino acid deletion. In especially preferred embodiments of the polypeptide, $X_5$ corresponds to the amino acid serine, $X_8$ corresponds to tyrosine, $X_9$ corresponds to glycine, $X_{10}$ corresponds to isoleucine, $X_{13}$ corresponds to isoleucine, $X_1$ corresponds to an amino acid deletion and $X_{15}$ corresponds to an amino acid deletion.

In another preferred embodiment of the polypeptide, $X_3$ corresponds to the amino acid serine, $X_5$ corresponds to serine, $X_8$ corresponds to tyrosine, $X_9$ corresponds to glycine, $X_{10}$ corresponds to isoleucine, $X_{13}$ corresponds to isoleucine, $X_1$ corresponds to an amino acid deletion and/or $X_{15}$ corresponds to an amino acid deletion. In especially preferred embodiments of the polypeptide, $X_3$ corresponds to the amino acid serine, $X_5$ corresponds to serine, $X_8$ corresponds to tyrosine, $X_9$ corresponds to glycine, $X_{10}$ corresponds to isoleucine, $X_{13}$ corresponds to isoleucine, $X_1$ corresponds to an amino acid deletion and/or $X_{15}$ corresponds to an amino acid deletion.

In an even more preferred embodiment of the polypeptide, $X_3$ corresponds to the amino acid serine, $X_5$ corresponds to serine, $X_8$ corresponds to proline, $X_9$ corresponds to glycine, $X_{10}$ corresponds to isoleucine, $X_{13}$ corresponds to isoleucine, $X_1$ corresponds to an amino acid deletion, $X_2$ corresponds to an amino acid deletion and/or $X_{15}$ corresponds to an amino acid deletion. In especially preferred embodiments of the polypeptide, $X_3$ corresponds to the amino acid serine, $X_5$ corresponds to serine, $X_8$ corresponds to proline, $X_9$ corresponds to glycine, $X_{10}$ corresponds to isoleucine, $X_{13}$ corresponds to isoleucine, $X_1$ corresponds to an amino acid deletion, $X_2$ corresponds to an amino acid deletion and $X_{15}$ corresponds to an amino acid deletion.

In another preferred embodiment of the polypeptide, $X_3$ corresponds to the amino acid serine, $X_5$ corresponds to serine, $X_8$ corresponds to tyrosine, $X_9$ corresponds to glycine, $X_{10}$ corresponds to isoleucine, $X_{12}$ corresponds to tyrosine, $X_{13}$ corresponds to isoleucine, $X_1$ corresponds to an amino acid deletion, $X_2$ corresponds to an amino acid deletion and/or $X_{15}$ corresponds to an amino acid deletion. In especially preferred embodiments of the polypeptide, $X_3$ corresponds to the amino acid serine, $X_5$ corresponds to serine, $X_8$ corresponds to tyrosine, $X_9$ corresponds to glycine, $X_{10}$ corresponds to isoleucine, $X_{12}$ corresponds to tyrosine, $X_{13}$ corresponds to isoleucine, $X_1$ corresponds to an amino acid deletion, $X_2$ corresponds to an amino acid deletion and $X_{15}$ corresponds to an amino acid deletion.

In additional preferred embodiments of the polypeptide, it is possible for the polypeptide to denote an amino acid sequence SEQ ID NO: 2 according to formula (2) as given below:

CKEYFYTSGKCSNPAVVFVTRC (2)     (SEQ ID NO: 2)

and/or the polypeptide of SEQ ID NO: 2 according to formula (2) may have at least one or more amino acid deletions, amino acid substitutions and/or amino acid insertions relative to the amino acid sequence SEQ ID NO: 2 according to formula (2).

The amino acid substitutions preferably relate to the sequence range of the ninth through twentieth amino acids of amino acid sequence SEQ ID NO: 2 according to formula (2), the range of amino acids glycine in position nine through threonine in position 20 of the amino acid sequence. Preferably one or more of the amino acids are selected from the group comprising glycine, cysteine, proline, valine, phenylalanine and/or alanine substituted by amino acids selected from the group comprising serine, tyrosine, isoleucine and/or glycine. One advantage of these amino acid substitutions is that they can enhance the stability at the polypeptide and/or can improve the antagonistic effect of the polypeptide.

These amino acid substitutions are preferably selected from substitutions comprising glycine for serine, nonterminal cysteine for serine, proline for tyrosine, valine for isoleucine, phenylalanine for tyrosine and/or alanine for glycine. These amino acid substitutions can be combined with one another in any desired manner.

It is preferred in particular for at least the nonterminal cysteine in position 11 of the amino acid sequence SEQ ID NO: 2 according to formula (2) to be replaced by serine. Such a substitution may advantageously result in an improvement in the solubility of the peptide, in particular its solubility in water.

It is especially preferable that in the embodiment of the polypeptide of amino acid sequence SEQ ID NO: 2 according to formula (2), the amino acid substitutions are preferably selected from the substitutions comprising glycine for serine, cysteine for serine and/or proline for tyrosine, which involve the $9^{th}$ through $14^{th}$ amino acids, the sequence range from glycine to proline of the amino acid sequence SEQ ID NO: 2 according to formula (2). This range preferably has at least one of these substitutions; preferably at least the cysteine in position 11 of the amino acid sequence SEQ ID NO: 2 according to formula (2) is substituted by serine. In additional preferred embodiments, proline is also replaced by tyrosine and/or glycine is replaced by serine. Substitution of cysteine in position 11 of the amino acid sequence may be combined with any other substitutions, in particular with substitution of proline for tyrosine and/or glycine for serine.

In these embodiments it is also preferred that amino acid substitutions involve the range of the $15^{th}$ through $20^{th}$ amino acids, alanine through threonine of the polypeptide of the amino acid sequence SEQ ID NO: 2 according to formula (2). Preferred amino acid substitutions of the amino acids of this range are selected from substitutions comprising alanine for glycine, valine for isoleucine and/or phenylalanine for tyrosine. It is especially preferable for alanine to be replaced by glycine. It is preferable for at least valine in position 16 of the amino acid sequence SEQ ID NO: 2 according to formula (2) to be replaced by isoleucine; preferably at least two of the valines are replaced by isoleucine; valines in positions 16 and 19 are preferably replaced by isoleucine. It may also be preferable for each valine of the amino acid sequence SEQ ID NO: 2 according to formula (2) to be replaced by isoleucine. In other preferred embodiments of the polypeptide, phenylalanine may be replaced by tyrosine.

Furthermore, in these embodiments, it is also preferable for alanine in position 15 of the sequence SEQ ID NO: 2 according to formula (2) to be replaced by glycine, for valine in position 16 to be replaced by isoleucine and valine in position 19 to be replaced by isoleucine. It has been found that these substitutions lead to a surprisingly stable polypeptide compound.

The substitutions and/or amino acid deletions may be combined in any desired manner; in particular the substitutions may be combined with one another in any manner.

Furthermore, the polypeptide in these embodiments may have deletions of amino acids. Preferred amino acid deletions involve deletions of the amino acids lysine, glutamine and/or arginine. The deletions preferably involve the amino acid lysine in position 2 of the sequence SEQ ID NO: 2 according to formula (2), the amino acid glutamine in position 3 and/or the amino acid arginine in position 21 of the amino acid sequence SEQ ID NO: 2 according to formula (2). These deletions may be combined in any manner. One amino acid is preferably deleted, but it is also possible to provide for lysine in position 2 as well as arginine in position 21 to be deleted. In additional embodiments, lysine in position 2, glutamine in position 3 and arginine in position 21 may be deleted.

Preferably no deletions are provided in the area of 4th through 20th amino acids of the amino acid sequence SEQ ID NO: 2 according to formula (2). In especially preferred embodiments, the amino acids in the area of the 4th through 8th amino acids are not affected by amino acid deletions or amino acid substitutions. As part of these investigations, it has been found that an amino acid sequence having at least two amino acid substitutions in the area of the 9th through 20th amino acids of the sequence SEQ ID NO: 2 according to formula (2), preferably three amino acid substitutions, more preferably four amino acid substitutions, even more preferably five amino acid substitutions in this area, will have good antagonistic properties.

The number of amino acids of the polypeptide of this embodiment is preferably in the range of ≧15 to ≦25 amino acids, [more] preferably in the range of ≧18 to ≦23 acids, especially preferably in the range of ≧19 to ≦22 amino acids, more preferably in the range of ≧20 to ≦21 amino acids, most especially preferably 22 amino acids.

An especially preferred embodiment of the polypeptide according to this invention, its pharmacologically acceptable salts, derivatives and/or conjugates has an amino acid sequence SEQ ID NO: 3 according to the following formula (3):

$$\text{CKEYFYTSGKSSNPGIVFITRC (3)} \qquad \text{(SEQ ID NO: 3)}$$

As part of these investigations it has been found that a polypeptide with an amino acid sequence SEQ ID NO: 3 as represented by formula (3) has an especially high antagonistic potential. It has been found in particular that the polypeptide may have a particularly good antagonistic effect. In particular, it has been found that a polypeptide with an amino acid sequence SEQ ID NO: 3 according to formula (3) can significantly and reproducibly inhibit the interaction of RANTES and PF4, which triggers potentiation of monocyte arrest.

It is particularly advantageous that a polypeptide of an amino acid sequence SEQ ID NO: 3 as represented in formula (3) can act specifically with respect to the interaction of RANTES and PF4. Further interference with the function of chemokines can thus be reduced or even prevented. This allows targeted use of the polypeptide in treatment of diseases, in particular cardiovascular diseases, associated with recruitment of monocytes or a RANTES-dependent recruitment of other leukocyte populations such as eosinophils.

Another preferred embodiment of the inventive polypeptide, its pharmacologically acceptable salts, derivatives and/or conjugates has an amino acid sequence SEQ ID NO: 4 according to formula (4) as given below:

$$\text{CEYFYTSGKSSNPGIVFITC (4)} \qquad \text{(SEQ ID NO: 4)}$$

Another preferred embodiment of the inventive polypeptide, its pharmacologically acceptable salts, derivatives and/or conjugates has an amino acid sequence SEQ ID NO: 5 according to formula (5) as given below:

$$\text{CEYFYTSGKSSNYGIVFITC (5)} \qquad \text{(SEQ ID NO: 5)}$$

Yet another preferred embodiment of the inventive polypeptide, its pharmacologically acceptable salts, derivatives and/or conjugates has an amino acid sequence SEQ ID NO: 6 according to the following formula (6) as given below:

$$\text{CEYFYTSSKSSNYGIVFITC (6)} \qquad \text{(SEQ ID NO: 6)}$$

An even more preferred embodiment of the inventive polypeptide, its pharmacologically acceptable salts, derivatives and/or conjugates has an amino acid sequence SEQ ID NO: 7 according to formula (7) as given below:

$$\text{CYFYTSSKSSNPGIVFITC (7)} \qquad \text{(SEQ ID NO: 7)}$$

One advantage of this polypeptide in preferred embodiments consists of the fact that these polypeptides preferably have an improved stability. This makes it possible for the polypeptides to reach their site of action to a greater extent and to enter into stable interactions with proteins or peptide compounds. In particular, an increased stability of the polypeptide allows it to be used in vivo and in vitro. Another advantage of the polypeptide in preferred embodiments lies in the fact that the polypeptide has an improved solubility in water. An increased solubility may in particular result in the polypeptide being easier and simpler to administer.

Furthermore, it is also possible for the respective L-amino acids to be replaced by D-amino acids. This can achieve a further increase in stability.

The polypeptides can be produced by the conventional methods of peptide synthesis.

The inventive polypeptides are advantageously suitable as an antagonist to the interaction between RANTES and platelet factor 4. In particular, the inventive polypeptides can induce inhibition of the interaction between RANTES and platelet factor 4.

The inventive polypeptides, their pharmacologically acceptable salts, derivatives and/or conjugates may be used as antagonists to the interaction between RANTES and platelet factor 4.

Owing to their advantageous properties, the inventive polypeptides are suitable for use as pharmaceutical drugs.

Another subject matter of the present invention relates to the use of the inventive polypeptides, in particular the preferred embodiments, for production of a pharmaceutical drug.

The inventive polypeptides can be administered according to conventional methods, but parenteral administration is preferred, e.g., oral administration [sic], dermal administration, subcutaneous administration and/or intravenous administration. For example, the polypeptides may be administered ex vivo administration, e.g., before implantation of a vascular interponate or by intravascular administration, e.g., before and after a catheter intervention or stent implantation. Good solubility of the polypeptides in water is a great advantage for such an application.

In addition to acute treatment or treatment for a limited period of time, it may also be preferable for the inventive polypeptides to be administered over a longer period of time. The inventive polypeptides may also be administered in the form of a sustained or delayed release, in the form of depot injections or osmotic pumps.

The inventive polypeptide may also be administered in the form of a nucleic acid coding for the respective polypeptide. The nucleic acid molecule here may be present in the conventional vectors. A DNA sequence coding for the respective polypeptide is preferably administered. It is also possible for the RNA coding for an inventive polypeptide to be administered.

Another subject matter of the invention is nucleic acids comprising nucleic acid sequences that code for the inventive polypeptides, preferably comprising nucleic acid sequences coding for polypeptides of the amino acid sequences SEQ ID NO: 1 according to formula (1), SEQ ID NO: 2 according to formula (2), SEQ ID NO: 3 according to formula (3), SEQ ID NO: 4 according to formula (4), SEQ ID NO: 5 according to formula (5), SEQ ID NO: 6 according to formula (6), SEQ ID NO: 7 according to formula (7). The nucleic acid that can be used according to this invention is preferably DNA or RNA. Those skilled in the art are familiar with DNA sequences that code for polypeptides according to the formulas, i.e., sequences give above.

One example of a nucleic acid molecule coding for a polypeptide of an amino acid sequence SEQ ID NO: 3 according to formula (3) has a DNA sequence SEQ ID NO: 8 according to formula (8) as given below:

```
                                              (SEQ ID NO: 8)
5'-TGCAAGGAATATTTCTACACTTCCGGGAAATCCTCCAATCC-

TGGAATTGTGTTCATCACTAGATGT-3' (8).
```

Those skilled in the art are familiar with other sequences which code for a polypeptide of an amino acid sequence SEQ ID NO: 3 according to formula (3). In addition, it is known that there may be changes in the sequence of the nucleic acids, e.g., due to degeneration of the genetic code.

One example of a nucleic acid molecule coding for a polypeptide of an amino acid sequence SEQ ID NO: 2 according to formula (2) has a DNA sequence SEQ ID NO: 9 according to formula (9) as given below:

```
                                              (SEQ ID NO: 9)
5'-TGCAAGGAATATTTCTACACTTCCGGGAAATGTTCCAATCCT-

GCCGTGGTGTTCGTCACTAGATGT-3' (9).
```

One example of a nucleic acid molecule coding for a polypeptide of an amino acid sequence SEQ ID NO: 4 according to formula (4) has a DNA sequence SEQ ID NO: 10 according to formula (10) as given below:

```
                                             (SEQ ID NO: 10)
5'-TGCGAATATTTCTACACTTCCGGGAAATCCTCCAATCCTGGAATT

GTGTTCATCACTTGT-3' (10).
```

One example of a nucleic acid molecule coding for a polypeptide of an amino acid sequence SEQ ID NO: 5 according to formula (5) has a DNA sequence SEQ ID NO: 11 according to formula (11) as given below:

```
                                             (SEQ ID NO: 11)
5'-TGCGAATATTTCTACACTTCCGGGAAATCCTCCAATTACGGAATT

GTGTTCATCACTTGT-3' (11).
```

One example of a nucleic acid molecule coding for a polypeptide of an amino acid sequence SEQ ID NO: 6 according to formula (6) has a DNA sequence SEQ ID NO: 12 according to formula (12) as given below:

```
                                             (SEQ ID NO: 12)
5'-TGCGAATATTTCTACACTTCCTCTAAATCCTCCAATTACGGAATT

GTGTTCATCACTTGT-3' (12).
```

One example of a nucleic acid molecule coding for a polypeptide of an amino acid sequence SEQ ID NO: 7 according to formula (7) has a DNA sequence SEQ ID NO: 13 according to formula (13) as given below:

```
                                             (SEQ ID NO: 13)
5'-TGCTATTTCTACACTTCCTCTAAATCCTCCAATCCTGGAATTGTG

TTCATCACTTGT-3' (13).
```

Those skilled in the art are familiar with other DNA sequences that code for polypeptides of an amino acid sequence SEQ ID NO: 1 according to formula (1), SEQ ID NO: 2 according to formula (2), SEQ ID NO: 3 according to formula (3), SEQ ID NO: 4 according to formula (4), SEQ ID NO: 5 according to formula (5), SEQ ID NO: 6 according to formula (6) and SEQ ID NO: 7 according to formula (7). Likewise, those skilled in the art are familiar with RNA sequences that code for polypeptides of an amino acid sequence SEQ ID NO: 1 according to formula (1), SEQ ID NO: 2 according to formula (2), SEQ ID NO: 3 according to formula (3), SEQ ID NO: 4 according to formula (4), SEQ ID NO: 5 according to formula (5), SEQ ID NO: 6 according to formula (6) and SEQ ID NO: 7 according to formula (7).

Preferred doses of the inventive polypeptides for administration to humans are in the range of $\geq$10 mg daily/75 kg body weight to $\leq$1000 mg daily/75 kg body weight, preferably in the range of $\geq$50 mg daily/75 kg body weight to $\leq$200 mg daily/75 kg body weight, preferably in the range of 150 mg daily/75 kg body weight.

The inventive polypeptides, their pharmacologically acceptable salts, derivatives and/or conjugates and/or nucleic acids can be used in particular for therapeutic and/or prophylactic treatment, diagnosis and/or treatment of diseases associated with recruitment of monocytes. These diseases include, for example, cardiovascular and/or inflammatory diseases, in particular arteriosclerosis, stenoses, hypertension and/or transplant rejection reactions.

The inventive polypeptides and/or nucleic acids are suitable in particular for treatment of mammals, in particular humans.

The inventive polypeptides can have a positive influence on the adhesion of monocytes to the endothelium. In particular, it has surprisingly been found that especially preferred embodiments of the inventive polypeptides can inhibit potentiation of such monocyte arrest mediated by the heterophilic interaction of RANTES and PF4. Especially preferred embodiments of the inventive polypeptides may advantageously yield an improved inhibition of potentiation of monocyte arrest mediated by the heterophilic interaction of RANTES and PF4 in experiments in comparison with what could be achieved with previously known protein or peptide compounds.

A special advantage of the inventive polypeptides can be achieved by the fact that the development of arteriosclerosis, postoperative or postinterventional restenoses, e.g., after balloon dilatation, atherectomy or bypass surgery can be reduced or prevented by administration of these polypeptides. It is a special advantage that the inventive polypeptides can prevent or reduce further recruitment of monocytes on activated endothelium even in advanced and/or clinical disease and/or morphological arteriosclerotic changes.

It is of particular advantage that the inventive polypeptides can be used in particular for prophylactic treatment, e.g., in patients at risk of hypertension. Such a prophylactic use is advantageously made possible in particular by the fact that the inventive polypeptides minor effects or none at all on general chemokine-mediated processes.

Another object of the present invention relates to the use of the inventive polypeptides, their pharmacologically acceptable salts, derivatives and/or conjugates for production of a pharmaceutical drug for therapeutic and/or prophylactic treatment of diseases, selected from the group comprising:

diseases associated with recruitment of monocytes such as cardiovascular and/or inflammatory diseases, in particular arteriosclerosis, atherosclerosis, unstable plaque, stenoses, restenoses, hypertension, arthritis, myocarditis, autoimmune diseases including encephalomyelitis, inflammatory intestinal diseases, reperfusion damage after infarction, e.g., myocardial or cerebral infarctions, transplant rejection and/or skin diseases such as psoriasis and/or diseases associated with a RANTES-dependent recruitment of other leukocyte populations such as eosinophilia, in particular in allergic diseases such as asthma or pneumonitis.

Especially in the treatment of atherosclerotic changes in humans, an advantageous effect on the course of the disease can be achieved by using the inventive polypeptides. In particular, a potentiation of the arteriosclerotic changes due to monocyte arrest can be reduced. Another advantage of the inventive polypeptides can be derived from the fact that these rejection reactions after transplantation of organs and/or tissue can be reduced or even prevented.

It is especially advantageous here that the inventive polypeptides preferably cause little or no adverse effects. This makes it possible for the inventive polypeptides to be administered prophylactically. In addition, it is especially advantageous that due to the specificity of the inventive polypeptides, an influence on other metabolic processes can be avoided, so that prophylactic administration, e.g., in patients at risk of hypertension or in prevention of arteriosclerotic changes is possible.

Another subject matter of the invention relates to pharmaceutical drugs comprising inventive polypeptides, preferably polypeptides of sequence SEQ ID NO: 1 according to formula (1), their pharmacologically acceptable salts, derivatives and/or conjugates. Pharmaceutical drugs comprising polypeptides selected from the group comprising polypeptides of amino acid sequences SEQ ID NO: 3 according to formula (3), SEQ ID NO: 4 according to formula (4), SEQ ID NO: 5 according to formula (5), SEQ ID NO: 6 according to formula (6) and/or SEQ ID NO: 7 according to formula (7) are preferred. Pharmaceutical drugs comprising polypeptides of the amino acid sequence SEQ ID NO: 3 according to formula (3) are especially preferred. The pharmaceutical drug preferably contains polypeptides according to one of the preceding formulas or SEQ ID numbers and it is also possible for the pharmaceutical drug to contain polypeptides according to several formulas or SEQ ID numbers.

Pharmaceutical drugs comprising inventive polypeptides can be used in particular for treatment in vivo in humans, for example. A preferred use of the pharmaceutical drugs comprising inventive polypeptides is for therapeutic and/or prophylactic treatment of diseases associated with recruitment of monocytes such as cardiovascular or inflammatory diseases in particular arteriosclerosis, atherosclerosis, unstable plaque, stenoses, restenoses, hypertension, arthritis, myocarditis, autoimmune diseases including encephalomyelitis, inflammatory intestinal diseases, reperfusion damage after infarctions, e.g., myocardial or cerebral infarctions, transplant rejection and/or skin diseases such as psoriasis and/or diseases associated with a RANTES-dependent recruitment of other leukocyte populations such as eosinophilia, in particular in allergic diseases such as asthma or pneumonitis.

Pharmaceutical drugs comprising nucleic acids coding for inventive polypeptides are also the subject matter of the present invention. The nucleic acid molecule may be present in conventional vectors.

Another subject matter of the present invention relates to agents to prevent monocyte arrest, comprising the inventive polypeptides, their pharmacologically acceptable salts, derivatives and/or conjugates, preferably comprising polypeptides or the amino acid sequence SEQ ID NO: 3 according to formula (3).

The term "agents to prevent monocyte arrest" in the sense of this invention means that agents can have a positive influence on diseases associated with monocyte arrest, adhesion of monocytes to endothelium, for example. In particular, the development of arteriosclerotic plaque can be reduced or even prevented. The use of the inventive polypeptides can preferably lead to a reduction and/or complete or almost complete prevention of the recruitment of monocytes and/or their adhesion to activated endothelium, in particular to arteriosclerotic plaque and/or neointima.

Examples that serve to illustrate the present invention are given below.

Materials and Methods

Cell Culture

Endothelial cells from the human umbilical cord (HUVEC, human umbilical vein endothelial cells, PromoCell, Heidelberg) were cultured in endothelial cell growth medium (PromoCell, Heidelberg) and used after two to four passages.

Monocytic Mono Mac 6 cells (MM6, DSMZ) were cultured in RPMI 1640 medium (PAA Laboratories, Pasching, Austria) with the addition of 10% fetal calf serum, 2 mM L-glutamine (Biowhittaker), 1 mM sodium pyruvate, 50 µg/mL gentamycin and 9 µg/mL insulin (MM6 medium). The cells were sown with a density of $2 \times 10^5$/mL in 2 mL MM6 medium in 24-well plates and cultured at 37° C. in a humid atmosphere with 5% $CO_2$ for 3 to 4 days before being used for experiments.

Polypeptides

Polypeptide of the sequence SEQ ID NO: 3 according to formula (3), its mouse ortholog according to the sequence SEQ ID NO: 15 according to formula (15) and a control peptide of the sequence SEQ ID NO: 14 according to formula (14) were synthesized chemically by means of t-Boc-based solid-phase peptide synthesis using 4-methylbenzhydrylamine resin, then purified by reverse phase HPLC and optionally cyclized in 6M guanidine HCl/Tris pH 8. The molecular weight was determined by means of electrospray mass spectrometry (Dawson, P. E., Kent, S. B. (2000), Annu. Rev. Biochem. 69:923-960; Hackeng, T. M., Griffin, J. H., Dawson, P. E. (1999), Proc. Natl. Acad. Sci. USA, vol. 96, pp. 10068-10073).

EXAMPLE 1

Plasmon Resonance Studies for Analysis of the Inhibitory Effect of the Polypeptide of the Sequence SEQ ID NO: 3 According to Formula (3) on the Formation of Heteroaggregates of RANTES and PF4

The plasmon resonance studies were performed using HBS-EP buffer (10 mM HEPES, 150 mM NaCl, 0.005% Tween 20, pH 7.4).

Two flow cells of a Cl chip (Biacore AB, Uppsala, Sweden) were activated by injection of 50 µL ethyl(dimethylaminopropyl)carbodiimide/N-hydroxysuccinimide (0.2M/0.05M, Pierce) and then 20 µL streptavidine (0.2 mg/mL, Sigma-Aldrich) was perfused over the activated surface. The surface was next inactivated by four successive injections of 20 µL ethylenediamine (1M, pH 8, Sigma-Aldrich).

Biotinylated human PF4 (bPF4) at the N-terminus was chemically synthesized by means of t-Boc-based solid phase peptide synthesis and native chemical ligation of PF4 (Dawson, P. E., Kent, S. B. (2000), Annu. Rev. Biochem. 69:923-960, Hackeng, T. M., Griffin, J. H., Dawson, P. E. (1999), Proc. Natl. Acad. Sci. USA, vol. 96, pp. 10068-10073). The bPF4 was immobilized on the dextran surface of a C1 sensor chip by injecting 200 µg/mL bPF4 into HBS-EP through one of the flow chambers and recorded 240 resonance units (RU). The second flow chamber was not treated with bPF4 and served as the reference.

Binding of RANTES (0.5 µM, recombinant human RANTES, Peprotech, Rocky Hill, N.J., USA) or RANTES (0.5 µM) that had been preincubated with various concentrations (0 µM, 10 µM and 100 µM) of the polypeptide of the sequence SEQ ID NO: 3 according to formula (3) in HBS-EP buffer overnight at room temperature to bPF4 was determined by injection of 15 µL of the respective peptide/RANTES mixture and observation of the binding for 180 seconds. The coupling was determined and the measurements were performed in a Biacore 2000 apparatus (Biacore AB) at a flow rate of 5 µL/min. Sensor grams of the RANTES binding were corrected using the BIAevaluation 3.0 software (Biacore AB) to correct for nonspecific background signals and equilibrium resonance units (RU) were determined for each injection.

It was found that the polypeptide of the sequence SEQ ID NO: 3 according to formula (3) was capable of inducing a concentration-dependent inhibition of the interaction of RANTES and PF4, whereby the binding of RANTES to immobilize PF4 were reduced by up to 35% in the presence of the peptide of the sequence SEQ ID NO: 3 according to formula (3) at a concentration of 100 µM.

EXAMPLE 2

Plasmon Resonance Studies for Analysis of the Inhibitory Effect of the Polypeptides of the Sequence SEQ ID NO: 3 According to Formula (3), SEQ ID NO: 2 According to Formula (2) and a Control Peptide for Binding of Heteroaggregates of RANTES and PF4

In another experiment under the same conditions as those described for example 1, the binding of RANTES (0.5 µM) or RANTES (0.5 µM) that had been preincubated with 0 µM, 10 µM, 50 µM and 100 µM of the polypeptide of the sequence SEQ ID NO: 3 according to formula (3), SEQ ID NO: 2 according to formula (2) or a control peptide of the sequence SEQ ID NO: 14 according to formula (14) as given below:

```
KEYFYTSGK (14)        (SEQ ID NO: 14)
``` was investigated.

In these experiments, it was found that at a concentration of 10 µM, 50 µM and 100 µM, the polypeptide of the sequence SEQ ID NO: 3 according to formula (3) was able to inhibit the interaction of RANTES and PF4 definitely more effective than the polypeptide of the sequence SEQ ID NO: 2 according to formula (2). The control peptide of the sequence SEQ ID NO: 14 according to formula (14) did not exhibit any detectable inhibition at a concentration of 100 µM.

EXAMPLE 3

Inhibition of Monocyte Arrest on Activated Endothelium

The interaction of monocytic Mono Mac 6 cells on activated endothelial cells was investigated.

Petri dishes with confluent HUVEC cells layers activated with IL-1β (Interleukin 1β, Peprotech, 10 ng/mL, 12 hours) were placed in a flow chamber. Mono Mac 6 cells ($0.5 \times 10^6$ cells/mL) were resuspended in balanced Hank solution (HBSS with 10 mM HEPES (Gibco BRL), pH 7.3, 0.5% bovine serum albumin (Serva)) and kept on ice. Five minutes before the experiment, $Ca^{2+}$ and $Mg^{2+}$ were added to the monocytic MM6 cells to yield a final concentration of 1 mM and 60 nM of the chemokines RANTES (Peprotech, Rocky Hill, N.J., USA) and PF4 (ChromaTec, Greifswald), respectively, and 6 µM of the polypeptides of the sequence SEQ ID NO: 2 according to formula (2), the sequence SEQ ID NO: 3 according to formula (3) or a control peptide of the sequence SEQ ID NO: 14 according to formula (14) and then heated up to 37° C. Cells pretreated in this way were then perfused over endothelial cells at 1.5 dyn/cm² on a microscope of model IX 50 from Olympus. The number of monocytes that were adherent due to the interaction with the endothelial cells was determined after 4 minutes in various fields by image analysis of photographs by a video camera (3CCD, JVC) and recorder. The data were analyzed as the mean (n=5)±standard deviation (p<0.02) in comparison with a control.

It was found that the potentiation of monocyte arrest due to the heterophilic interaction of RANTES and PF4 was inhibited significantly, e.g., up to 80% by the polypeptide of the sequence SEQ ID NO: 3 according to formula (3), whereas inhibition by the polypeptide of the sequence SEQ ID NO: 2 according to formula (2) was weaker. The control peptide of the sequence SEQ ID NO: 14 according to formula (14), however, had no significant inhibition.

EXAMPLE 4

In Vivo Experiments in a Mouse Model of Artherosclerosis [Sic; Atherosclerosis]

The model for artherosclerosis [sic; atherosclerosis] was 9- to 12-week-old female ApoE litter-mate mice (The Jackson Lab, Bar Harbor, Me., USA). The mice were fed a high-fat diet (21% fat, Altromin® C1061) for 12 weeks. During this period of time, two groups of mice received intraperitoneal injections of 50 µg of the polypeptide of the sequence SEQ ID NO: 15 according to formula (15), administered three times a week, as indicated below:

```
CKEYFYTSSKSSNLAVVFVTRC (15)    (SEQ ID NO: 15)
```

(n=12 mice) or corresponding injections of a control peptide of the sequence SEQ ID NO: 14 according to formula (14) as given below:

```
KEYFYTSGK (14)        (SEQ ID NO: 14)
```

(n=7 mice) in saline solution. An untreated group of mice (n=12) was used as additional controls.

The mice were sacrificed for histological examination. During the experimental period, the mice were healthy and did not show any signs of disease. Blood samples were taken at the beginning and end of the experimental nutrition period. The white blood cell count was determined by hemocytometry and the sera were collected, the cholesterol using the Infinity cholesterol kits (Thermo Electron, Melbourne, Australia).

The extent of the atherosclerosis was determined at the aortic route and on thoracoabdominal aorta by staining lipid deposits using Oil Red O staining (N. R. Veillard, B. Kwak, G. Pelli, F. Mulhaupt, R. W. James, A. E. Proudfoot, F. Mach, Antagonism of RANTES receptors reduces atherosclerotic plaque formation in mice. Circ. Res. 2004; 94:253-61) and quantified by means of computerized image analysis (Diskus software, Hilgers, Aachen). Areas of atherosclerotic lesions were determined in 5 µm transverse sections through the heart and aortic root. The determination was performed for each aortic root on the basis of lipid stained areas of six sections a distance of 50 µm apart. The areas of atherosclerotic lesions were divided by the total surface area of the valve of each section. The thoracoabdominal aorta was opened along the ventral midline and the areas of the lesions were stained in an en-face preparation using Oil Red-O staining. The proportional amount of lipid deposit was calculated by dividing the stained area by the total thoracoabdominal surface area.

It was found that the mice that had been treated with the polypeptide of the sequence SEQ ID NO: 15 according to formula (15), the mouse ortholog of the polypeptide of the sequence SEQ ID NO: 3 according to formula (3) showed a significant reduction in the development of atherosclerotic lesions in comparison with the mice that had received the control peptide. In addition it was found that the area of the aortic root showing plaque was significantly reduced in relation to the total valve surface area in the treated mice. It was also found that the macrophage content in the lesions was significantly reduced.

It was thus demonstrated that the development of atherosclerosis in vivo could be delayed by the mouse ortholog of the polypeptide of the sequence SEQ ID NO: 3 according to formula (3) and the inventive polypeptides are thus suitable for therapeutic use.

The invention claimed is:

1. A cyclic polypeptide, its pharmacologically acceptable salts, derivatives, and/or conjugates, consisting of the formula (1):

(SEQ ID NO: 1)
C-X1-X2-YFYTS-X3-X4-X5-X6-X7-X8-X9-X10-X11-X12-X13-X14-X15-C (1)

wherein:
X1 is selected from the group consisting of: lysine, glutamine, arginine, histidine and asparagine, or an amino acid deletion;
X2 is selected from the group consisting of: glutamic acid, aspartic acid and glutamine, or an amino acid deletion;
X3 is selected from the group consisting of: glycine, serine and alanine;
X4 is selected from the group consisting of: lysine, leucine and arginine;
X5 is selected from the group consisting of: serine, cysteine, glycine and threonine;
X6 is selected from the group consisting of: serine, glycine and threonine;
X7 is selected from the group consisting of: asparagine and glutamine;
X8 is selected from the group consisting of: proline, tyrosine and glycine;
X9 is selected from the group consisting of: glycine, alanine and serine;
X10 is selected from the group consisting of: isoleucine, valine and asparagine;
X11 is selected from the group consisting of: valine, isoleucine and asparagine;
X12 is selected from the group consisting of: phenylalanine, tyrosine, isoleucine, valine, leucine and methionine;
X13 is selected from the group consisting of: isoleucine, valine, leucine, methionine and phenylalanine;
X14 is selected from the group consisting of: threonine, glycine, alanine, serine and tyrosine;
X15 is selected from the group consisting of: arginine, lysine, glutamine, histidine and asparagine, or an amino acid deletion.

2. The cyclic polypeptide of claim 1, wherein the polypeptide comprises between 19 and 22 amino acids.

3. The cyclic polypeptide of claim 1, wherein:
X1 is lysine or an amino acid deletion;
X2 is glutamic acid or an amino acid deletion;
X3 is glycine or serine;
X5 is serine;
X8 is proline or tyrosine;
X9 is glycine;
X10 is isoleucine;
X12 is phenylalanine or tyrosine;
X13 is isoleucine; and
X15 is arginine or an amino acid deletion.

4. The cyclic polypeptide of claim 3, consisting of the sequence:

(SEQ ID NO: 2)
CKEYFYTSGKCSNPAVVFVTRC.

5. The cyclic polypeptide of claim 1, consisting of the sequence:

(SEQ ID NO: 3)
CKEYFYTSGKSSNPGIVFITRC.

6. The cyclic polypeptide of claim 1, consisting of the sequence:

(SEQ ID NO: 4)
CEYFYTSGKSSNPGIVFITC.

7. The cyclic polypeptide of claim 1, consisting of the sequence:

(SEQ ID NO: 5)
CEYFYTSGKSSNYGIVFITC.

8. The cyclic polypeptide of claim 1, consisting of the sequence:

(SEQ ID NO: 6)
CEYFYTSSKSSNYGIVFITC.

9. The cyclic polypeptide of claim 1, consisting of the sequence:

(SEQ ID NO: 7)
CYFYTSSKSSNPGIVFITC.

10. The cyclic polypeptide of claim 1, consisting of the sequence:

(SEQ ID NO: 16)
CKEYFYTSGKSSNPAVVFVTRC.

11. A pharmaceutical composition, comprising (a) a cyclic polypeptide of claim 1, its pharmacologically acceptable salts, derivatives and/or conjugates, and (b) a pharmaceutically-acceptable excipient.

12. A method of antagonizing interaction between the protein Regulated upon Activation, Normal T-cell Expressed, and Secreted (RANTES and platelet factor 4 (PF4), comprising contacting PF4 with a cyclic polypeptide of claim 1.

13. The method of claim 12, wherein the contacting occurs in vivo.

14. A method of treating atherosclerosis, comprising administering to an individual in need thereof a cyclic polypeptide of claim 1.

* * * * *

SEQUENCE LISTING

```
<160> NUMBER OF SEQ ID NOS: 16

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Gln, Arg, His, Asn, or not present
<220> FEATURE:
<221> NAME/KEY: MOD_RES
<222> LOCATION: (3)..(3)
<223> OTHER INFORMATION: Glu, Asp, Gln, or not present
<220> FEATURE:
<221> NAME/KEY: MOD_RES
<222> LOCATION: (9)..(9)
<223> OTHER INFORMATION: Gly, Ser, or Ala
<220> FEATURE:
<221> NAME/KEY: MOD_RES
<222> LOCATION: (10)..(10)
<223> OTHER INFORMATION: Lys, Leu, or Arg
<220> FEATURE:
<221> NAME/KEY: MOD_RES
<222> LOCATION: (11)..(11)
<223> OTHER INFORMATION: Ser, Cys, Gly, or Thr
<220> FEATURE:
<221> NAME/KEY: MOD_RES
<222> LOCATION: (12)..(12)
<223> OTHER INFORMATION: Ser, Gly, or Thr
<220> FEATURE:
<221> NAME/KEY: MOD_RES
<222> LOCATION: (13)..(13)
<223> OTHER INFORMATION: Asn or Gln
<220> FEATURE:
<221> NAME/KEY: MOD_RES
<222> LOCATION: (14)..(14)
<223> OTHER INFORMATION: Pro, Tyr, or Gly
<220> FEATURE:
<221> NAME/KEY: MOD_RES
<222> LOCATION: (15)..(15)
<223> OTHER INFORMATION: Gly, Ala, or Ser
<220> FEATURE:
<221> NAME/KEY: MOD_RES
<222> LOCATION: (16)..(16)
<223> OTHER INFORMATION: Ile, Val, or Asn
<220> FEATURE:
```

```
<221> NAME/KEY: MOD_RES
<222> LOCATION: (17)..(17)
<223> OTHER INFORMATION: Val, Ile, or Asn
<220> FEATURE:
<221> NAME/KEY: MOD_RES
<222> LOCATION: (18)..(18)
<223> OTHER INFORMATION: Phe, Tyr, Ile, Val, Leu, or Met
<220> FEATURE:
<221> NAME/KEY: MOD_RES
<222> LOCATION: (19)..(19)
<223> OTHER INFORMATION: Ile, Val, Leu, Met, or Phe
<220> FEATURE:
<221> NAME/KEY: MOD_RES
<222> LOCATION: (20)..(20)
<223> OTHER INFORMATION: Thr, Gly, Ala, Ser, or Tyr
<220> FEATURE:
<221> NAME/KEY: MOD_RES
<222> LOCATION: (21)..(21)
<223> OTHER INFORMATION: Arg, Lys, Gln, His, Asn, or not present
<220> FEATURE:
<223> OTHER INFORMATION: see specification as filed for detailed
      description of substitutions and preferred embodiments

<400> SEQUENCE: 1

Cys Xaa Xaa Tyr Phe Tyr Thr Ser Xaa Xaa Xaa Xaa Xaa Xaa Xaa
1               5                   10                  15

Xaa Xaa Xaa Xaa Xaa Cys
            20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Lys Glu Tyr Phe Tyr Thr Ser Gly Lys Cys Ser Asn Pro Ala Val
1               5                   10                  15

Val Phe Val Thr Arg Cys
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Lys Glu Tyr Phe Tyr Thr Ser Gly Lys Ser Ser Asn Pro Gly Ile
1               5                   10                  15

Val Phe Ile Thr Arg Cys
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Glu Tyr Phe Tyr Thr Ser Gly Lys Ser Ser Asn Pro Gly Ile Val
1               5                   10                  15

Phe Ile Thr Cys
```

-continued

```
<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Glu Tyr Phe Tyr Thr Ser Gly Lys Ser Ser Asn Tyr Gly Ile Val
1               5                   10                  15

Phe Ile Thr Cys
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Glu Tyr Phe Tyr Thr Ser Ser Lys Ser Ser Asn Tyr Gly Ile Val
1               5                   10                  15

Phe Ile Thr Cys
            20

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Tyr Phe Tyr Thr Ser Ser Lys Ser Ser Asn Pro Gly Ile Val Phe
1               5                   10                  15

Ile Thr Cys

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgcaaggaat atttctacac ttccgggaaa tcctccaatc ctggaattgt gttcatcact    60
agatgt                                                              66

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgcaaggaat atttctacac ttccgggaaa tcctccaatc ctgccgtggt gttcgtcact    60
```

-continued agatgt          66

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgcgaatatt tctacacttc cgggaaatcc tccaatcctg gaattgtgtt catcacttgt          60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcgaatatt tctacacttc cgggaaatcc tccaattacg gaattgtgtt catcacttgt          60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcgaatatt tctacacttc ctctaaatcc tccaattacg gaattgtgtt catcacttgt          60

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgctatttct acacttcctc taaatcctcc aatcctggaa ttgtgttcat cacttgt          57

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Glu Tyr Phe Tyr Thr Ser Gly Lys
1               5

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Lys Glu Tyr Phe Tyr Thr Ser Ser Lys Ser Ser Asn Leu Ala Val

```
1               5                   10                  15
Val Phe Val Thr Arg Cys
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Lys Glu Tyr Phe Tyr Thr Ser Ser Gly Ser Ser Asn Pro Ala Val
1               5                   10                  15

Val Phe Val Thr Arg Cys
            20
```